(12) United States Patent
Brinker et al.

(10) Patent No.: US 10,433,891 B2
(45) Date of Patent: Oct. 8, 2019

(54) APPARATUS, SYSTEM, AND METHOD FOR ANCHORING CABLE TO BONE

(71) Applicant: Cable Fix LLC, Hernando, MS (US)

(72) Inventors: Mark Brinker, Houston, TX (US); William Ricci, Richmond Heights, MO (US); Carey Bryant, Hernando, MS (US)

(73) Assignee: CABLE FIX LLC, Hernando, MS (US)

( * ) Notice: Subject to any disclaimer, the term of this patent is extended or adjusted under 35 U.S.C. 154(b) by 879 days.

(21) Appl. No.: 14/961,386

(22) Filed: Dec. 7, 2015

(65) Prior Publication Data

US 2017/0156772 A1    Jun. 8, 2017

(51) Int. Cl.
*A61B 17/04* (2006.01)
*A61B 17/86* (2006.01)
*A61F 2/08* (2006.01)
*A61B 17/88* (2006.01)

(52) U.S. Cl.
CPC ........ *A61B 17/862* (2013.01); *A61B 17/8645* (2013.01); *A61B 17/8883* (2013.01)

(58) Field of Classification Search
None
See application file for complete search history.

(56) References Cited

U.S. PATENT DOCUMENTS

| | | |
|---|---|---|
| 479,938 A | 8/1892 | Fredlihp |
| 899,612 A | 9/1908 | Phillips |
| 3,166,072 A | 1/1965 | Sullivan, Jr. |
| 4,060,089 A | 11/1977 | Noiles |
| 4,532,927 A | 8/1985 | Miksza, Jr. |
| 4,534,350 A | 8/1985 | Golden et al. |
| 4,534,352 A | 8/1985 | Korthoff |
| 4,548,202 A | 10/1985 | Duncan |
| 4,573,469 A | 3/1986 | Golden et al. |
| 4,610,250 A | 9/1986 | Green |
| 4,754,758 A | 7/1988 | Lehmann |
| 4,932,960 A | 6/1990 | Green |
| 5,358,510 A | 10/1994 | Luscombe et al. |
| 5,478,353 A | 12/1995 | Yoon |
| 5,620,452 A | 4/1997 | Yoon |
| 5,665,109 A | 9/1997 | Yoon |
| 5,797,932 A | 8/1998 | Min et al. |
| 5,984,001 A | 11/1999 | Larsen et al. |
| 6,276,032 B1 | 8/2001 | Nortman et al. |
| 6,712,830 B2 | 3/2004 | Esplin |

(Continued)

*Primary Examiner* — Sameh R Boles
(74) *Attorney, Agent, or Firm* — Kunzler Bean & Adamson (57) ABSTRACT

An apparatus for anchoring cable to bone includes an anchor configured to be anchored in a bone and a cable fixed to the anchor. The cable is configured to be tensioned to a measurable and adjustable tension to cause a measurable and adjustable compression of the bone by the cable. The apparatus may include a cable housing having a proximal portion, a distal portion, and a passage. The distal portion is detachably and co-rotatably engageable with the anchor and the passage is open to and extends from a distal end of the distal portion. The apparatus also includes a cable having a fixed-end portion and a free-end portion. The fixed-end portion of the cable is fixed to the anchor and the free-end portion of the cable is non-fixedly positionable in the passage of the cable housing.

14 Claims, 8 Drawing Sheets

(56) References Cited

U.S. PATENT DOCUMENTS

| | | |
|---|---|---|
| 6,966,919 B2 | 11/2005 | Sixto et al. |
| 7,033,378 B2 | 4/2006 | Smith et al. |
| 7,094,251 B2 | 8/2006 | Bonutti et al. |
| 7,678,122 B2 | 3/2010 | Kortenbach et al. |
| 7,854,750 B2 | 12/2010 | Bonutti et al. |
| 7,985,241 B2 | 7/2011 | Smith et al. |
| 8,080,020 B2 | 12/2011 | Kortenbach et al. |
| 8,114,100 B2 | 2/2012 | Smith et al. |
| 8,162,977 B2 | 4/2012 | Bonutti et al. |
| 8,454,628 B2 | 6/2013 | Smith et al. |
| 8,613,750 B2 | 12/2013 | Smith et al. |
| 9,039,596 B2 | 5/2015 | Sater |
| 9,220,503 B2 | 12/2015 | Ranchod |
| 9,788,827 B2 | 10/2017 | Miksza et al. |
| 2001/0051815 A1 | 12/2001 | Esplin |
| 2002/0029044 A1 | 3/2002 | Monassevitch et al. |
| 2004/0044366 A1 | 3/2004 | Bonutti et al. |
| 2004/0059349 A1 | 3/2004 | Sixto et al. |
| 2004/0059354 A1 | 3/2004 | Smith et al. |
| 2004/0059358 A1 | 3/2004 | Kortenbach et al. |
| 2007/0032825 A1 | 2/2007 | Bonutti et al. |
| 2008/0046007 A1 | 2/2008 | Schwemberger et al. |
| 2008/0046008 A1 | 2/2008 | Smith et al. |
| 2008/0097430 A1 | 4/2008 | Bernstein et al. |
| 2008/0108897 A1 | 5/2008 | Bonutti et al. |
| 2008/0140095 A1 | 6/2008 | Smith et al. |
| 2008/0147116 A1 | 6/2008 | Smith et al. |
| 2008/0149685 A1 | 6/2008 | Smith et al. |
| 2010/0179568 A1 | 7/2010 | Kortenbach et al. |
| 2010/0198258 A1 | 8/2010 | Heaven et al. |
| 2011/0040307 A1 | 2/2011 | Ranchod |
| 2011/0092993 A1 | 4/2011 | Jacobs |
| 2011/0201877 A1 | 8/2011 | Sater |
| 2012/0065638 A1 | 5/2012 | Moore |
| 2012/0130374 A1 | 5/2012 | Bouduban et al. |
| 2012/0143247 A1 | 6/2012 | Smith et al. |
| 2014/0364905 A1* | 12/2014 | Lunn .................. A61B 17/0401 606/232 |
| 2016/0081686 A1 | 3/2016 | Miksza et al. |
| 2016/0100835 A1 | 4/2016 | Linder et al. |
| 2016/0346023 A1 | 12/2016 | Bouduban et al. |
| 2017/0156738 A1 | 6/2017 | Ricci et al. |
| 2017/0156771 A1 | 6/2017 | Brinker et al. |
| 2017/0156774 A1 | 6/2017 | Bryant et al. |
| 2017/0156775 A1 | 6/2017 | Bryant et al. |
| 2017/0156779 A1 | 6/2017 | Bryant et al. |
| 2017/0156847 A1 | 6/2017 | Ricci et al. |
| 2018/0055550 A1 | 3/2018 | Bryant et al. |

* cited by examiner

APPARATUS, SYSTEM, AND METHOD FOR ANCHORING CABLE TO BONE

FIELD

The subject matter of the present disclosure relates generally to anchoring cable to bone. More specifically, the present disclosure relates to installing an anchor with a pre-attached cable into bone.

BACKGROUND

Various medical procedures utilize cables or conventional sutures to secure damaged skeletal tissue or soft tissue. Tissues, such as bones or soft-tissues, that have been fragmented, fractured, broken, torn, pulled, stretched, or otherwise damaged need to be set and held in specific orientations in order to properly heal. Cables or conventional sutures may be useful for securing/attaching torn tissue back together or facilitating holding bone fragments in place. However, conventional tools and procedures for utilizing cables or conventional sutures in medical surgeries are generally time-consuming, complex, and usually involve multiple in-situ steps that are difficult to perform.

SUMMARY

From the foregoing discussion, it should be apparent that a need exists for an apparatus, system, and method for anchoring cable to bone that overcome the limitations of conventional medical tools and procedures. Beneficially, such an apparatus, system, and method would improve the ease, efficiency, and effectiveness of medical procedures that involve anchoring cable to bone.

The subject matter of the present application has been developed in response to the present state of the art, and in particular, in response to the problems and needs in the art that have not yet been fully solved by currently available medical tools and procedures. Accordingly, the present disclosure has been developed to provide an apparatus for anchoring cable to bone, and its related systems and methods, that overcome many or all of the above-discussed shortcomings in the art.

According to one embodiment, an apparatus for anchoring cable to bone includes an anchor configured to be anchored to a bone and a cable fixed to the anchor, wherein the cable is configured to be tensioned to a measurable and adjustable tension to cause a measurable and adjustable compression of the bone by the cable.

Disclosed herein is one embodiment of an apparatus for anchoring cable to bone. The apparatus includes an anchor configured to be anchored in a bone, a cable housing having a proximal portion, a distal portion, and a passage. The distal portion is detachably and co-rotatably engageable with the anchor and the passage is open to and extends from a distal end of the distal portion. The apparatus also includes a cable having a fixed-end portion and a free-end portion. The fixed-end portion of the cable is fixed to the anchor and the free-end portion of the cable is non-fixedly positionable in the passage of the cable housing.

According to one implementation, the anchor has a shank with a non-circular outer-periphery that is engageable with a complementary non-circular interior surface of the passage of the cable housing. In such an implementation, the shank of the anchor is at least partially receivable within the passage of the distal portion of the cable housing. In another implementation, the proximal portion of the cable housing is detachably coupleable to a driving tool. In yet another implementation, the passage is open to a proximal end of the proximal portion of the cable housing and the passage extends longitudinally through the cable housing and has a proximal opening at the proximal end and a distal opening at the distal end. In such an implementation, the cable housing further includes a cap detachably engageable with the proximal end to cover the proximal opening, with the cap being configured to retain the free-end portion of the cable within the passage of the cable housing. The cap may also have a connection feature mateable to a driving tool.

In one implementation, the free-end portion of the cable is coiled within the passage. For example, an internal cross-sectional area of a proximal section of the passage in the proximal portion of the cable housing may be larger than an internal cross-sectional area of a distal section of the passage in the distal portion of the cable housing so that the free-end portion of the cable can be coiled within the proximal section of the passage.

In one implementation, the distal portion of the cable housing has cutting features disposed on an external surface of the distal portion. The cutting features are configured to counter-sink the bone. In another implementation, the anchor has a threaded portion with a plurality of external threads that secure the anchor to the bone. The threaded portion of the anchor may further include a cutting portion that cuts through the bone (with or without a pilot hole). The cable 140 may be made from any one of various materials. For example, in specific implementations, the cable 140 is made from metal, such as stainless steel, titanium, or other metal.

Also disclosed herein is another embodiment of an apparatus for anchoring cable to bone. The apparatus includes an anchor having a shank and a threaded portion. The anchor is configured to be anchored in a bone, the shank has a non-circular outer-periphery, and the threaded portion has a cutting portion. The apparatus further includes a cable housing that includes a proximal portion, a distal portion, and passage. The passage is open to and extends longitudinally between a proximal end of the proximal portion and a distal end of the distal portion. The passage has a non-circular inner surface complementing the non-circular outer-periphery of the shank of the anchor. The distal portion of the cable housing is detachably and co-rotatably engageable with the shank of the anchor via engagement of the non-circular inner surface with the non-circular outer-periphery. Still further, the apparatus includes a cable that has a fixed-end portion and a free-end portion. The fixed-end portion of the cable is fixed to the shank of the anchor. The proximal section of the passage in the proximal portion of the cable housing has a comparatively larger cross-section than a distal section of the passage in the distal portion. Also, the free-end portion of the cable is coiled within the proximal section of the passage. The apparatus further includes a cap detachably engageable with the proximal end to cover the proximal opening. The cap is configured to retain the free-end portion of the cable within the passage of the cable housing.

In one implementation, the distal portion of the cable housing includes cutting features configured to counter-sink the bone. The cutting features are disposed on an external surface of the distal portion of the cable housing.

According to one embodiment, a method for anchoring cable to bone includes a cable fixed to the anchor, wherein the cable is configured to be tensioned to a measurable and adjustable tension to cause a measurable and adjustable compression of the bone by the cable. The method also includes with the anchor at least partially embedded in the bone, tensioning the cable to a measurable and adjustable tension.

Disclosed herein is one embodiment of a method for anchoring cable to bone. The method includes releasably attaching a distal portion of a cable housing to an anchor. The cable is fixed to the anchor, the cable housing has a passage, and the cable is non-fixedly positioned in the passage. After attaching the distal portion of the cable housing to the anchor, the method includes co-rotating the cable housing and the anchor to drive the anchor into a bone. The method subsequently includes withdrawing the cable housing away from the bone to collectively detach the anchor from the cable housing and remove the cable from the passage of the cable housing.

According to one implementation, the anchor includes a shank and attaching the distal portion of the cable housing to the anchor includes engaging a non-circular outer-periphery of a shank of the anchor with a non-circular inner surface of the distal portion of the cable housing. In another implementation, co-rotating the cable housing and the anchor includes mating the proximal portion of the cable housing with a driving tool and actuating the driving tool to drive the anchor into the bone. In a further implementation, the distal portion of the cable housing has cutting features and co-rotating the cable housing and the anchor to drive the anchor into a bone includes counter-sinking the bone with the cutting features. According to yet another implementation, the method further includes loading the cable into the passage of the cable housing before co-rotating the cable housing and the anchor. In a further implementation, the method includes passing the cable through a cable hole of a soft-tissue fixation device before tensioning the cable.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the subject matter disclosed herein. Thus, discussion of the features and advantages, and similar language, throughout this specification may, but do not necessarily, refer to the same embodiment.

Furthermore, the described features, advantages, and characteristics of the disclosure may be combined in any suitable manner in one or more embodiments. One skilled in the relevant art will recognize that the subject matter of the present application may be practiced without one or more of the specific features or advantages of a particular embodiment. In other instances, additional features and advantages may be recognized in certain embodiments that may not be present in all embodiments of the disclosure. Further, in some instances, well-known structures, materials, or operations are not shown or described in detail to avoid obscuring aspects of the subject matter of the present disclosure. These features and advantages of the present disclosure will become more fully apparent from the following description and appended claims, or may be learned by the practice of the disclosure as set forth hereinafter.

BRIEF DESCRIPTION OF THE DRAWINGS

In order that the advantages of the disclosure will be readily understood, a more particular description of the disclosure briefly described above will be rendered by reference to specific embodiments that are illustrated in the appended drawings. Understanding that these drawings depict only typical embodiments of the disclosure and are not therefore to be considered to be limiting of its scope, the subject matter of the present application will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

In the following description, numerous specific details are provided. One skilled in the relevant art will recognize, however, that the subject matter of the present application may be practiced without one or more of the specific details, or with other methods, components, materials, and so forth. In other instances, well-known structures, materials, or operations are not shown or described in detail to avoid obscuring aspects of the disclosure. Also, like reference numbers (e.g., 120 and 220) refer to like components (e.g., different embodiments of the same component).

Illustrated in FIGS. 1-7 are several representative embodiments of an apparatus 100 for anchoring cable to bone. As described herein, the apparatus for anchoring cable to bone provides various advantages and benefits over other medical tools and procedures. However, the recited advantages are not meant to be limiting in any way, as one skilled in the art will appreciate that other advantages may also be realized upon practicing the present disclosure.

FIGS. 1-4 are perspective views of the apparatus 100 for anchoring cable to bone. The apparatus 100 includes an anchor 120, a cable 140, and a cable housing 160. The anchor 120 has a threaded portion 122 and a shank 124. The cable 140 has a fixed-end portion 142 and a free-end portion 144. The cable housing 160 has a distal portion 162, a proximal portion 164, and a passage 166. The shank 124 of the anchor 120 is detachably and co-rotatably engageable with the distal portion 162 of the cable housing 160. Also, the fixed-end portion 142 of the cable 140 is fixedly coupled to the shank 124 of the anchor 120 while the free-end portion 144 of the cable 140 is non-fixedly positioned in the passage 166 of the cable housing 160.

Figure 5A:
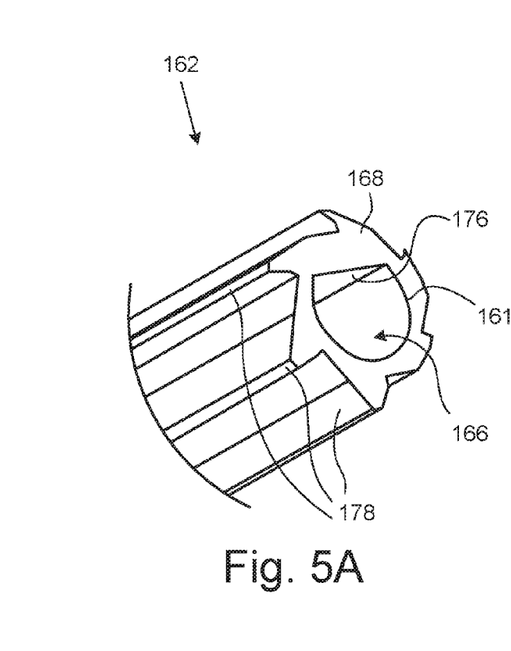
FIG. 5A is a perspective view of a distal portion of the cable housing, according to one embodiment.

The cable housing is at least partially hollow. In one embodiment, the passage 166 is a central chamber of the at least partially hollow cable housing 160. In another embodiment, the passage is not centrally located in the cable housing but instead is offset from center. As shown in FIG. 5, the passage 166 is open to and extends from a distal opening 161 at the distal end 168 of the distal portion 162 of the cable housing 160.

The cable housing 160 and the anchor 120 are detachably and co-rotatably coupled together so that rotation of the cable housing 160 causes the anchor 120 to also rotate. In other words, the cable housing 160 and the anchor 120 are coupleable to co-rotate together. A practitioner may engage the proximal portion 164 of the cable housing 160, either manually using a hand tool or indirectly using a power tool, to rotate the cable housing 160. Accordingly, the cable housing may include external engagement features, either disposed on the surface of the proximal portion 164 (e.g., hexagonal nut feature) or disposed on the proximal end 169 (e.g., chuck feature, shank feature, etc.) of the cable housing 160. When a practitioner engages the external engagement feature, the cable housing 160 and the anchor are co-rotatably coupled together and rotation of the cable housing 160 causes the anchor 120 to also rotate.

Figure 1:
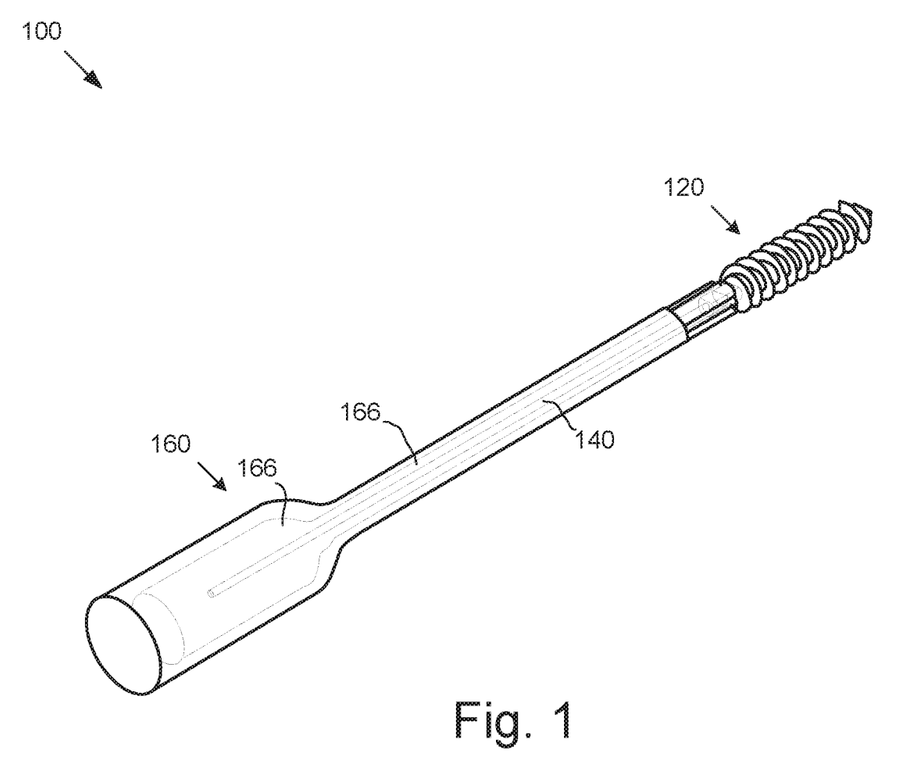
FIG. 1 is a perspective view of an apparatus for anchoring cable to bone, with a cable positioned within a passage of a cable housing, according to one embodiment.
Figure 2:
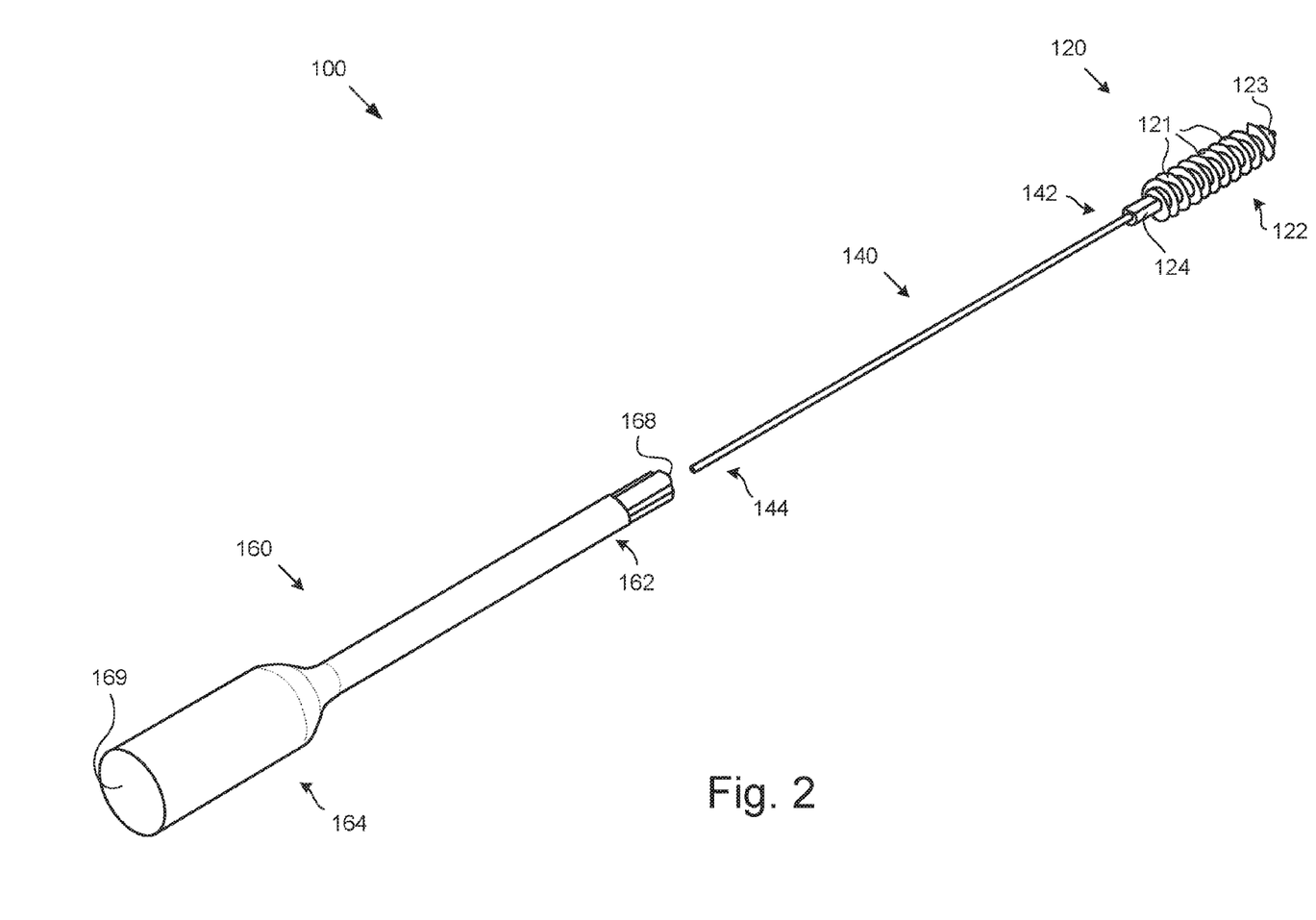
FIG. 2 is a perspective view of the apparatus of FIG. 1 but with the cable withdrawn from the passage of the cable housing, according to one embodiment.
Figure 3:
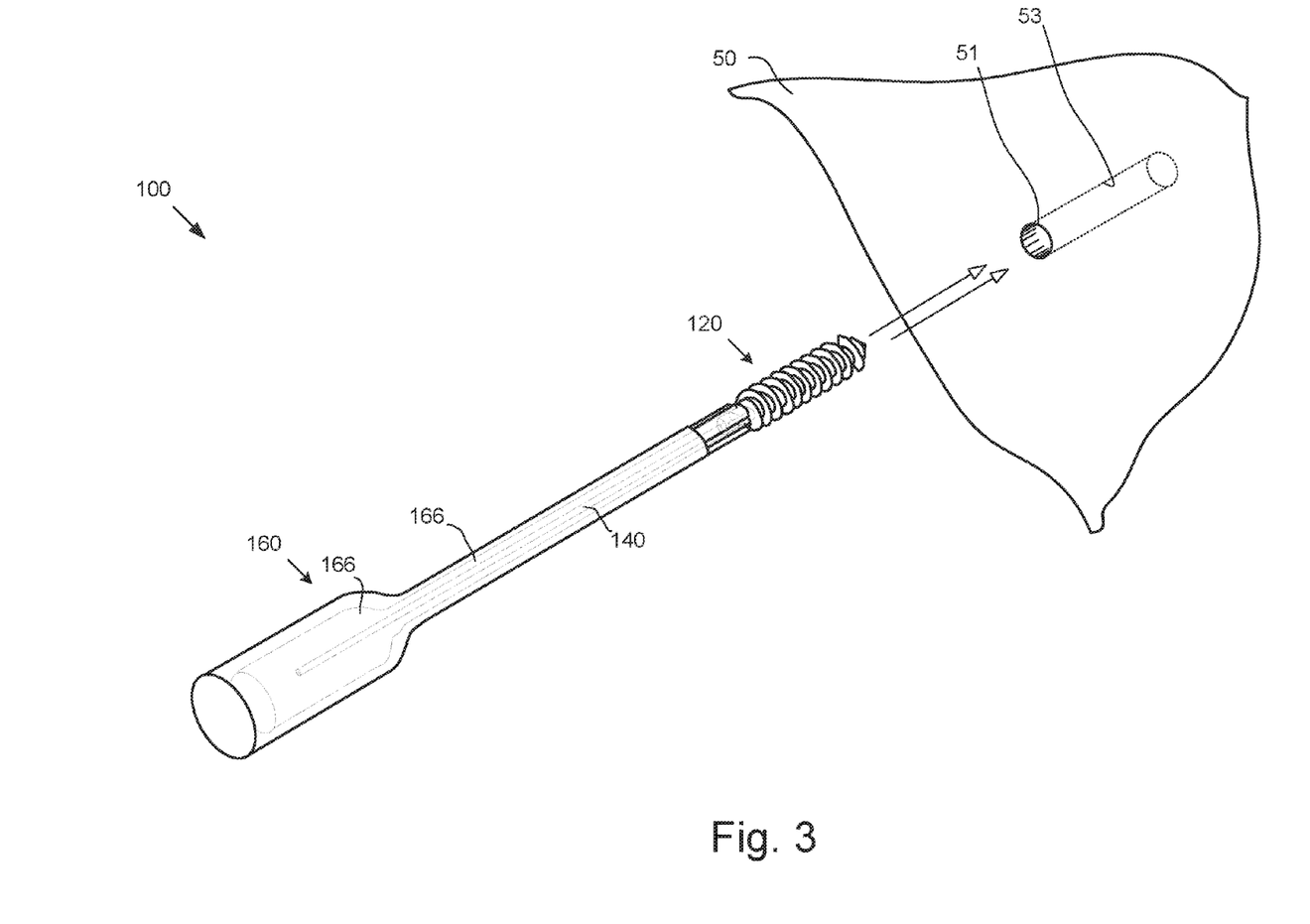
FIG. 3 is a perspective view of the apparatus before installing an anchor into a hole in a bone, according to one embodiment.
Figure 4:
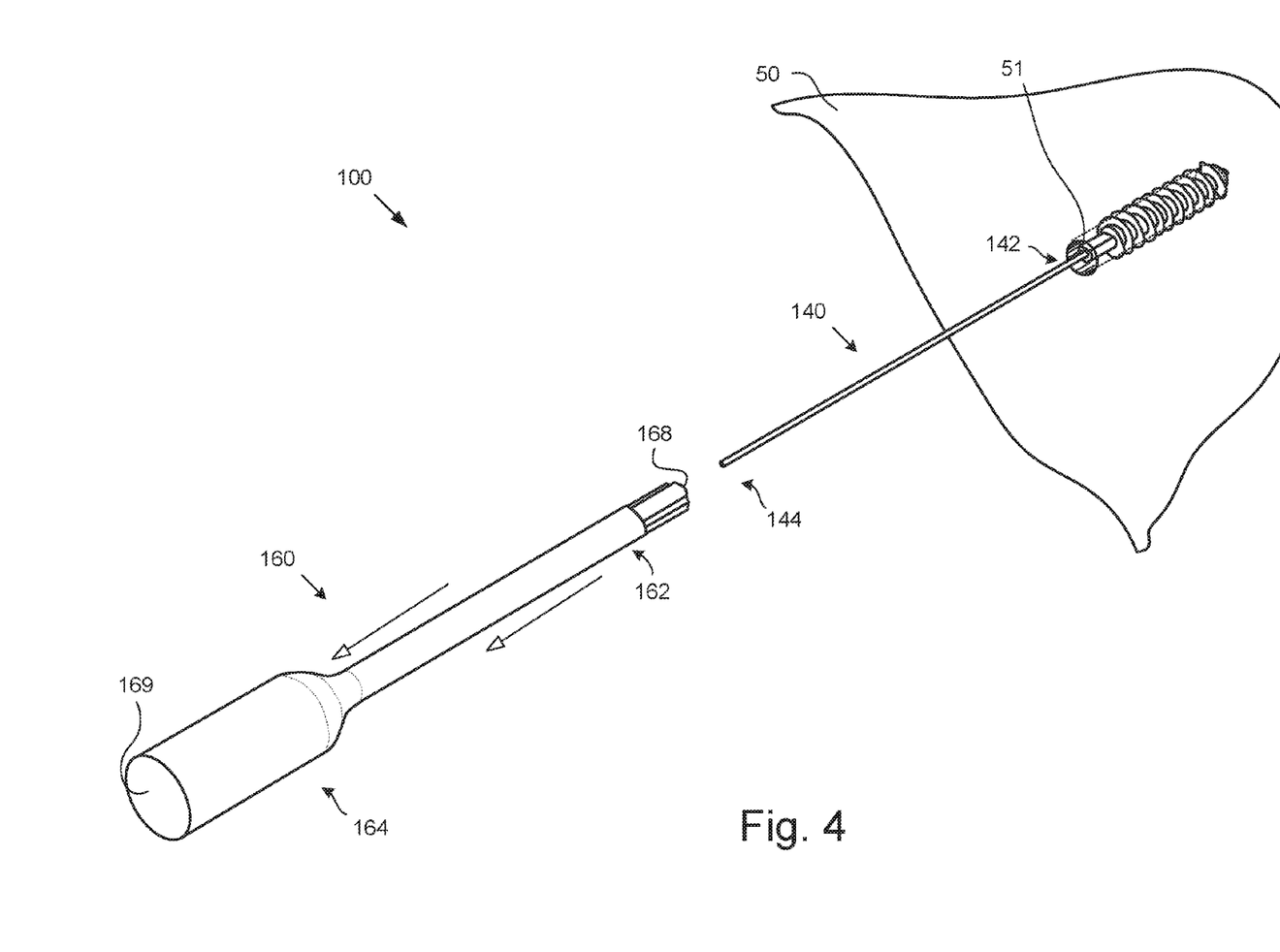
FIG. 4 is a perspective view of the apparatus, with the anchor secured to the bone and the cable withdrawn from the passage of the cable housing, according to one embodiment.

As shown in FIG. 2, the threaded portion 122 of the anchor 120 includes a cutting portion 123 and a plurality of external threads 121. The cutting portion 123 of the anchor 120 cuts into bone 50 as the anchor 120 rotates. In one embodiment, as depicted in FIGS. 3 and 4, the bone 50 already has a preformed hole 51 and the anchor 120 can be secured to the bone by being driven into the pilot hole 51 so that the external threads 121 securely engage the bone 50. In another embodiment, the bone does not have a pre-drilled hole and the cutting portion 123 of the anchor 120 drills and cuts into the bone 50 with the threads securely embedding in the side 53 of the hole 51 in the bone 50.

As described above, the fixed-end portion 142 of the cable 140 is permanently fixed to the shank 124 of the anchor 120 while the free-end portion 144 is positionable within the passage 166 of the cable housing 160. Once the anchor 120 has been securely anchored/embedded within the bone 50 by co-rotating the cable housing 160 and the anchor 120, the cable housing 160 may be detached from the shank 124 of the anchor 120 and the cable housing 160 may be withdrawn from the bone 50, thereby exposing the free-end portion 144 of the cable 140. The free-end portion 144 of the cable 140 can be used in a medical procedure or a surgery to hold skeletal tissue or soft-tissue in a desired position to allow the body of a patient to properly heal. For example, the cable 140 may be wrapped and tensioned around bone or soft-tissue, similar to a cerclage wire configuration. In another implementation, the free-end portion 144 of the cable 140 may be inserted through a through-hole (e.g., a tunnel, passage, or passageway) in a bone. Further, the cable 140 may be tensioned to a measurable and adjustable tension in order to facilitate reducing and stabilizing bone fractures or to facilitate the repair of dislocations or soft-tissue damage. In some implementations, tensioning the cable 140 to a measurable and adjustable tension causes a measurable and adjustable compression of the bone by the cable.

The anchor 120 may be made from stainless steel or titanium. In another embodiment, the anchor 120 may be made from low carbon steel, high carbon steel, high speed steel, cobalt steel alloys, tungsten carbide, and polycrystalline diamond, among other materials. In a further embodiment, the anchor 120 may be made from a ceramic material or a bio-absorbable material. The anchor 120 may also have one or more coatings to prevent corrosion, or improve the cutting and anchoring performance of the anchor 120. The coating, which may be antimicrobial, may also be useful to decrease the likelihood of toxicity and infection in the bone tissue.

According to one embodiment, the term "cable" refers to a cord-like element, such as a wire, filament, weave, or thread, whether bundled or individual, that is capable of holding a measurable and adjustable tension and causing a measurable and adjustable compression of bone. In other words, the tension in the cable can be measured, such as by a tension measuring device, and can be adjusted, such as after an initial tensioning of the cable. When used to compress bone (e.g., to compress two bone segments together), the measured tension in the cable is equal to a measured compression of the bone. Thus, as used herein, a measured and adjustable tension of a cable is synonymous with a measured and adjustable compression of bone by the cable.

In one embodiment, the measurable and adjustable tension may be a specific, known, predictable, expected, controllable, anticipated, desired, repeatable, sustainable, and/or predeterminable tension. For example, the cable 140 may be passed through a pass-through hole in a bone and may be tensioned to a measurable and adjustable tension in order to facilitate the reduction and fixation of fractures or to otherwise facilitate the repair of dislocations or soft-tissue damage. In other words, the cable 140 is not a conventional suture or conventional thread material, since such materials are incapable of, or at least not well-suited for, maintaining a measurable and adjustable tension. Thus, the term "cable" refers to a flexible yet substantially non-stretchable element that can be tensioned to a measurable and adjustable tension. In such an embodiment, because the cable 140 is capable of maintaining or retaining a measurable and adjustable tension, the effectiveness and reproducibility of successful surgical procedures is improved. In other words, different surgical procedures relating to different bones in the body may involve different degrees of retention/fixation force (e.g., the fixation force required to reduce a fracture in the femur may be greater than the fixation force required to reduce a fracture in the patella). Accordingly, the ability of the cable 140 to be tensioned to a measurable and adjustable tension improves the reliability and reproducibility of surgical procedures when compared with other medical procedures that do not utilize cables. The cable 140 may be made from any one of various materials. For example, in specific implementations, the cable 140 is made from metal, such as stainless steel, titanium, or other metal.

The cable housing 160 may be made from various materials, including metals such as stainless steel and synthetics such as a rigid plastic, polymer, or composite. In one embodiment, the cable housing 160 is disposable. In another embodiment, the cable housing 160 may be sterilized, a new cable 140 may be loaded into the passage 166, and the cable housing 160 may be re-used. In one embodiment, as depicted in the figures, the proximal portion 164 of the cable housing 160 may have a comparatively larger external cross-sectional dimension than the distal portion 162 of the cable housing 160. However, in another embodiment, the cable housing 160 may have an external cross-sectional dimension that is substantially uniform along the entire length of the cable housing 160. Further, while the cross-sectional shape of the cable housing 160 is depicted as having a circular cross-sectional shape (e.g., a cylindrical), in other embodiments the cable housing 160 may have a rectangular or polygonal cross-sectional shape. Additional details regarding the anchor 120, the cable 140, and the cable housing 160 of the apparatus 100 are included below with reference to the remaining figures.

Figure 5B:
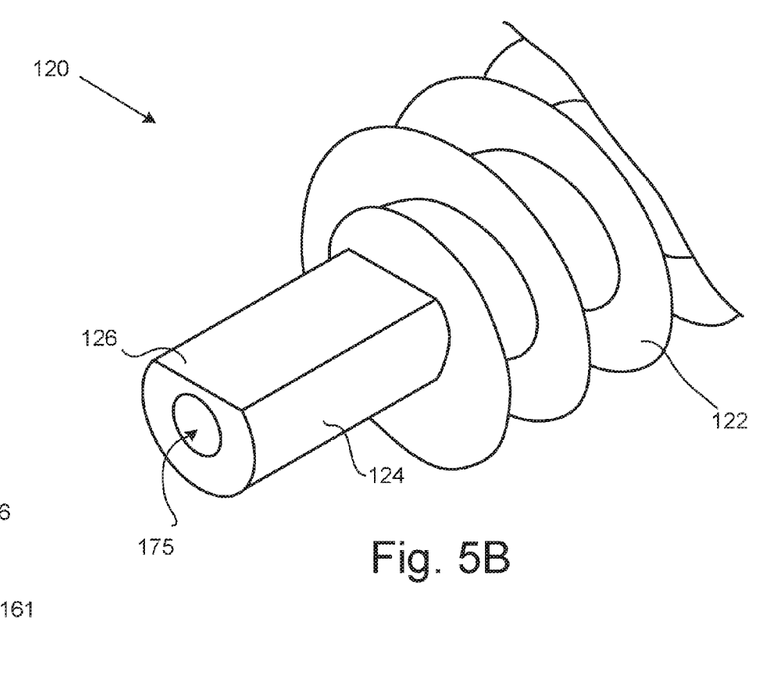
FIG. 5B is a perspective view of a shank of an anchor, according to one embodiment.

FIG. 5A is a distal perspective view of the distal portion 162 of the cable housing 160 and FIG. 5B is a proximal view of the shank 124 of the anchor 120. As mentioned above, the cable housing 160 is detachably and co-rotatably engageable with the anchor 120. In the embodiment depicted in FIGS. 5A and 5B, the shank 124 has a non-circular outer-periphery 126 that is engageable with a complementary non-circular interior surface 176 of the passage 166 at the distal portion 162 of the cable housing 160. In other words, the shank 124 of the anchor 120 is at least partially receivable through the distal opening 161 at the distal end 168 of the distal portion 162 of the cable housing 160 so that the shank 124 engages the interior surface 176 of the passage 166.

The non-circular but respectively conforming or complementary shape of the shank 124 of the anchor 120 and the distal portion 162 of the cable housing 160 enables the co-rotation of the two components 120, 160. In another embodiment, the detachable and co-rotatable engagement between the anchor 120 and the cable housing 160 may be accomplished using other configurations. For example, a tongue and groove configuration or a pin and bore configuration, among others, may be implemented to form the engagement between the anchor 120 and the cable housing 160.

The fixed-end portion 142 of the cable 140 is permanently coupled to the anchor 120. In one embodiment, the fixed-end portion 142 of the cable 140 may be inserted into a bore 175 in the shank 124 of the anchor 120. The fixed-end portion 142 of the cable 140 may be crimped, glued, welded, or otherwise fixed to the shank 124 of the anchor 120.

According to the embodiment depicted in FIG. 5A, the distal portion 162 of the cable housing 160 includes cutting features 178. The cutting features 178 are configured to counter-sink the bone. In one embodiment, at least a section of the distal portion of the cable housing may have a cross-sectional dimension that is small enough to fit within the hole 51, thus allowing the anchor 120 to be driven to a desired depth within the bone 50. In another embodiment, the cable housing 160 may include a flange or other stop-feature that prevents too much of the cable housing 160 from entering the hole 51, thus effectively restricting the depth of the anchor 120 within the bone 50.

Figure 6:
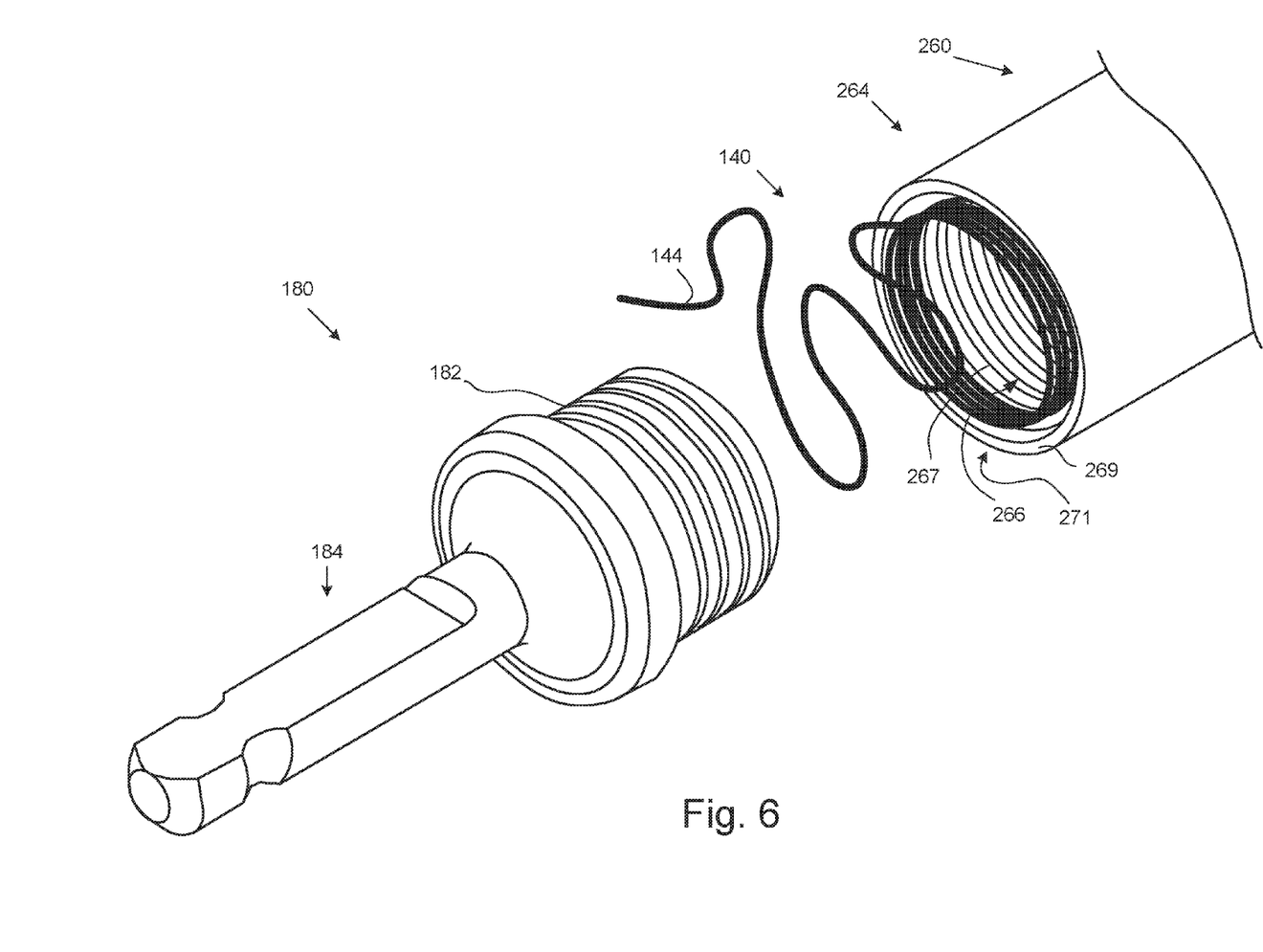
FIG. 6 is a perspective view of a proximal portion of the cable housing, with a detachable cap detachably engageable to the cable housing, according to one embodiment.

FIG. 6 is a perspective view of the proximal portion 264 of the cable housing 260 with a cap 180 detachably engageable with the cable housing 260. As shown in the depicted embodiments, the cable housing 260, in addition to the distal opening 161 at the distal end 168 (see, e.g., FIG. 5A), also has a proximal opening 271 at the proximal end 269 of the proximal portion 264. In other words, the passage 266 extends longitudinally within the cable housing 260 and has a proximal opening 271 at the proximal end 269 and a distal opening 161 at the distal end 168. The proximal portion 264 of the cable housing 260 may also have internal threads 267 that are threadably engageable with external threads 182 of the cap 180. As shown, the cap 180 may also include a connection feature (e.g., shank) 184 that is engageable/mateable with a driving tool or other surgical tool for driving the rotation of the cable housing 260.

In one embodiment, the loading of the cable 140 into the passage 266 may be facilitated by the cap 180. For example, connecting the cap 180 to cover the proximal opening 271 may securely hold the free-end portion 144 of the cable 140 within the passage. In one embodiment, the free-end portion 144 of the cable 140 is coiled within the passage 266.

Figure 7:
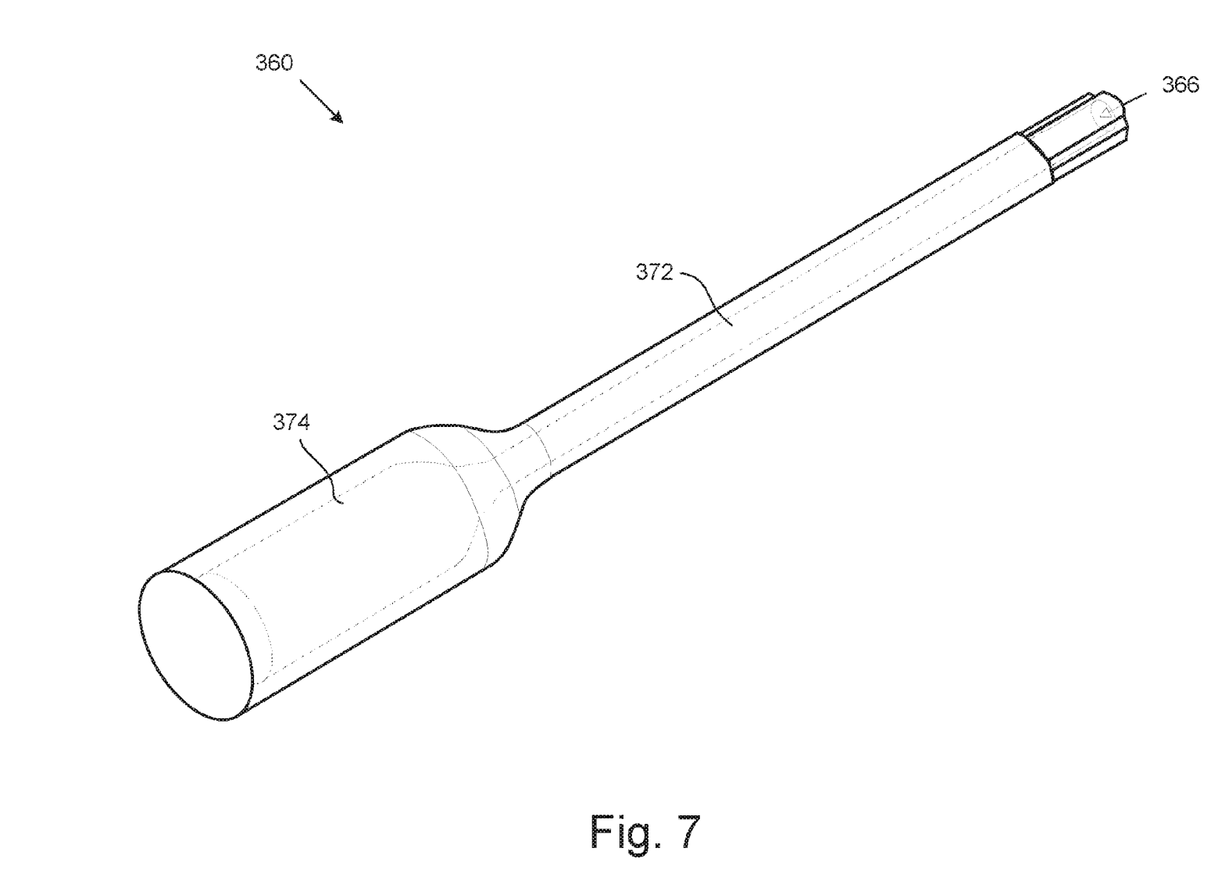
FIG. 7 is a perspective view of the cable housing, according to one embodiment.

FIG. 7 is a perspective view of one embodiment of the cable housing 360 showing the passage 366 having a proximal section 374 and a distal section 372. As described above, the external cross-sectional dimension of the cable housing may change along the length of the cable housing, according to the specifics of a given use. For example, the external dimensions of the cable housing 160 may be selected based on the type of driving tool used and/or the insertion depth of the anchor within the bone, among other considerations. Similarly, according to the embodiment shown in FIG. 7, the interior dimensions of the passage 366 may vary along the length of the passage 366. For example, the cable 140 may be coiled or otherwise packed within the proximal section 374 of the passage 366. The distal section 372 of the passage 366 may be configured to have an internal dimension that is just larger than the external diameter of the cable 140.

Figure 8:
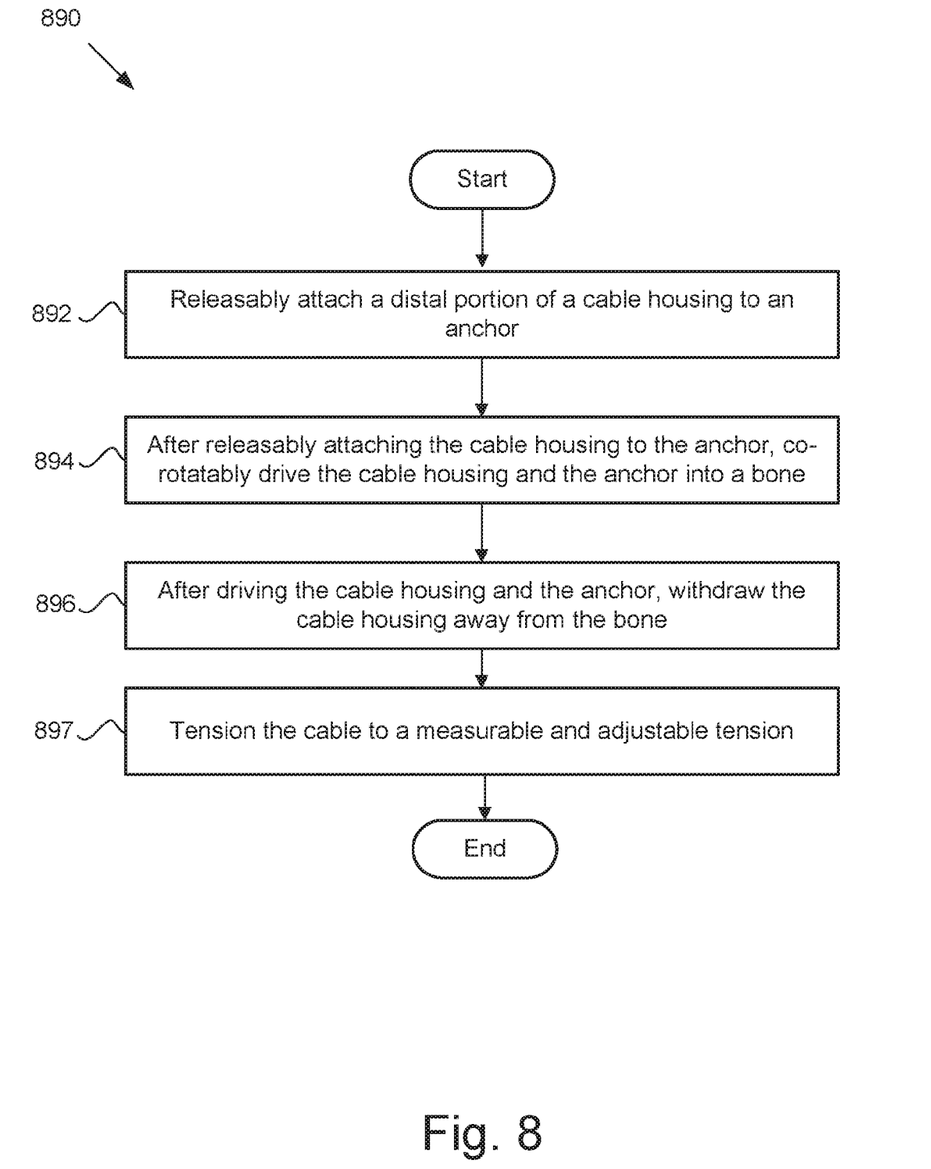
FIG. 8 is a schematic flowchart diagram of a method for anchoring cable to bone, according to one embodiment.

FIG. 8 is a schematic flowchart diagram of one embodiment of a method 890 for anchoring the cable 140 to bone 50. Generally, the method 890 includes at least partially embedding an anchor in bone and tensioning a cable, fixedly attached to the anchor, to a measurable and adjustable tension to cause, in some implementations, a measurable and adjustable compression of the bone by the cable. The cable can be pre-attached to the anchor prior to embedding the anchor in bone, or attached to the anchor after the anchor is embedded in bone. In specific implementations, the method 890 includes releasably attaching the distal portion of the cable housing to the anchor at 892. Attaching the cable housing to the anchor may involve engaging the non-circular outer-periphery of the shank of the anchor with the non-circular inner surface of the distal portion of the cable housing. The fixed-end portion of the cable is fixed to the anchor and the free-end portion of the cable is non-fixedly positioned in the passage. After attaching the distal portion of the cable housing to the anchor, the method 890 includes co-rotating the cable housing and the anchor to drive the anchor into a bone at 894. Driving the anchor into the bone at 894 can be performed with or without a pilot hole.

Subsequently, the method 890 includes withdrawing the cable housing away from the bone to collectively detach the anchor from the cable housing and remove the cable from the passage of the cable housing at 896. The method 890 further includes tensioning the cable to a measurable and adjustable tension at 897, which may occur after withdrawing the cable housing at 896. According to an optional step of the method 890, after the cable is tensioned to a measurable and adjustable tension, the method can include releasing the tension in the cable and re-tensioning the cable to the same or different measurable and adjustable tension. Releasing the tension in the cable may include unlocking a lock that is configured to maintain the cable in tension. The ability to release tension in a cable and subsequently re-tension the cable provides various advantages, such as, for example, facilitating re-use of the cable on other targeted areas of the body in one or more subsequent procedures, in some implementations, and adjustment to the tension or position of the cable on the same targeted area of the body in the same or a subsequent procedure, in other implementations.

In one embodiment, co-rotating the cable housing and the anchor at 894 includes mating the proximal portion of the cable housing with a driving tool and actuating the driving tool to drive the anchor into the bone. In another embodiment, co-rotating the cable housing and the anchor at 894 further includes counter-sinking the bone with the cutting features disposed on the external surface of the distal portion of the cable housing. In another embodiment, before co-rotating the cable housing and the anchor at 894, the method 890 includes loading the cable into the passage of the cable housing. In yet another embodiment, the method 890 includes co-rotating the cable housing and the anchor in an opposite direction to remove the anchor from the bone. The method 890 may further include wrapping the cable around the bone before tensioning the cable. In another embodiment, the method 890 may include passing the cable through a pass-through hole in bone before tensioning the cable.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C; or some other suitable combination. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The subject matter of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. An apparatus for anchoring cable to bone, the apparatus comprising: an anchor configured to be anchored to a bone; a cable fixed to the anchor, wherein the cable is configured to be tensioned to a measurable and adjustable tension to cause a measurable and adjustable compression of the bone by the cable; a cable housing comprising a proximal portion, a distal portion, and a passage, wherein: the distal portion is detachably and co-rotatably engageable with the anchor; and the passage is open to and extends from a distal end of the distal portion; wherein the cable comprises a fixed-end portion and a free-end portion, the fixed-end portion of the cable being fixed to the anchor and the free-end portion of the cable being non-fixedly positionable in the passage of the cable housing, wherein the anchor comprises a shank, wherein the shank has a non-circular outer-periphery that is engageable with a complementary non-circular interior surface of the passage of the cable housing.

2. The apparatus of claim 1, wherein the shank of the anchor is at least partially receivable within the passage of the distal portion of the cable housing.

3. The apparatus of claim 1, wherein the proximal portion of the cable housing is detachably coupleable to a driving tool.

4. The apparatus of claim 1, wherein:
the passage is open to a proximal end of the proximal portion of the cable housing; and
the passage extends longitudinally through the cable housing and has a proximal opening at the proximal end and a distal opening at the distal end.

5. The apparatus of claim 4, wherein:
the cable housing further comprises a cap detachably engageable with the proximal end to cover the proximal opening; and
the cap is configured to retain the free-end portion of the cable within the passage of the cable housing.

6. The apparatus of claim 5, wherein the cap comprises a connection feature mateable to a driving tool.

7. The apparatus of claim 2, wherein the free-end portion of the cable is coiled within the passage.

8. The apparatus of claim 7, wherein:
a cross-sectional area of a proximal section of the passage in the proximal portion of the cable housing is larger than a cross-sectional area of a distal section of the passage in the distal portion of the cable housing; and
the free-end portion of the cable is coiled within the proximal section of the passage.

9. The apparatus of claim 1, wherein the distal portion of the cable housing comprises cutting features configured to counter-sink the bone.

10. The apparatus of claim 1, wherein the anchor comprises a threaded portion with a plurality of external threads.

11. The apparatus of claim 10, wherein the threaded portion of the anchor comprises a cutting portion.

12. The apparatus of claim 1, wherein the cable is made from a metal material.

13. An apparatus for anchoring cable to bone, the apparatus comprising:
an anchor comprising a shank and a threaded portion, wherein:
the anchor is configured to be anchored in a bone;
the shank has a non-circular outer-periphery; and
the threaded portion comprises a cutting portion;
a cable housing comprising a proximal portion, a distal portion, and passage, wherein:
the passage is open to and extends longitudinally between a proximal end of the proximal portion and a distal end of the distal portion;
the passage has a non-circular inner surface complementing the non-circular outer-periphery of the shank of the anchor; and
the distal portion of the cable housing is detachably and co-rotatably engageable with the shank of the anchor via engagement of the non-circular inner surface with the non-circular outer-periphery;
a cable comprising a fixed-end portion and a free-end portion, wherein:
the fixed-end portion of the cable is fixed to the shank of the anchor;
a proximal section of the passage in the proximal portion of the cable housing has a comparatively larger cross-section than a distal section of the passage in the distal portion; and
the free-end portion of the cable is coiled within the proximal section of the passage; and
a cap detachably engageable with the proximal end to cover the proximal opening, wherein the cap is configured to retain the free-end portion of the cable within the passage of the cable housing.

14. The apparatus of claim 13, wherein the distal portion of the cable housing comprises cutting features configured to counter-sink the bone.

* * * * *